United States Patent
Li et al.

(10) Patent No.: US 6,980,624 B2
(45) Date of Patent: Dec. 27, 2005

(54) NON-UNIFORM VIEW WEIGHTING TOMOSYNTHESIS METHOD AND APPARATUS

(75) Inventors: Baojun Li, Waukesha, WI (US); Bernhard Erich Hermann Claus, Niskayuna, NY (US); Gopal B. Avinash, New Berlin, WI (US); Stephen W. Metz, Greenfield, WI (US); Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 117 days.

(21) Appl. No.: 10/723,034

(22) Filed: Nov. 26, 2003

(65) Prior Publication Data

US 2005/0111616 A1 May 26, 2005

(51) Int. Cl.[7] ............................................. A61B 6/03
(52) U.S. Cl. .................................. 378/23; 378/22
(58) Field of Search .............................. 378/4, 21, 22, 378/23, 901

(56) References Cited

U.S. PATENT DOCUMENTS

| 6,542,570 B1 * | 4/2003 | Silver .............................. 378/4 |
| 6,778,630 B2 * | 8/2004 | Silver et al. .................... 378/15 |
| 2003/0123614 A1 * | 7/2003 | Silver et al. ................. 378/146 |

* cited by examiner

Primary Examiner—David V Bruce
(74) Attorney, Agent, or Firm—Fletcher Yoder (57) ABSTRACT

A technique is provided for non-uniform weighting in back-projection calculations in tomosythesis. The non-uniform weighting may include weighting based on a count map of the number of times pixels of individual slices are traversed by radiation in different projections. Weighting may also include non-uniform functions for contributions of features at different slice level to the sensed X-ray attenuation system response inconsistencies are accounted for by further weighting based upon projection maps which may be created in separate system calibration or configuration routines.

21 Claims, 4 Drawing Sheets

NON-UNIFORM VIEW WEIGHTING TOMOSYNTHESIS METHOD AND APPARATUS

BACKGROUND OF THE INVENTION

The present invention relates generally to tomosynthesis imaging systems. More particularly, the invention relates to a technique for correcting or avoiding certain artifacts and generally improving tomosynthesis images by use of non-uniform view weighting.

Tomosynthesis systems have developed over the past decades and now offer significant advantages for many types of imaging, such as in the medical diagnostics field. In general, X-ray tomosynthesis involves the use of low dose X-ray radiation to produce a series of images acquired over a range of X-ray beam orientations relative to an image object. In currently available systems the object is positioned in front of a digital detector and the X-ray source is moved to various positions to produce the series of images. A number of such images may be produced, typically in excess of 50 or 60. The detector collects electrical data representative of the depletion of a charge at individual pixel locations resulting from continuation of the X-ray radiation at those locations by intervening objects, such as the features of the images subject, a patient in the medical diagnostics context, for example. Acquiring images of the subject from a different orientations of the X-ray beam allows depth information to be incorporated into the final 3D image. The depth information is unavailable in conventional projection X-ray imaging, making tomosynthesis attractive for identifying specific features of interest and their general location within the subject.

Amorphous silicon flat panel digital X-ray detectors are currently available for tomosynthesis imaging. In general, however, any X-ray detector that provides a digital projection image may be used. These may include, for example, charge coupled device (CCD) arrays, digitized film screens, or other digital detectors, such as direct conversion detectors. The low electronic noise and fast read-out times of such detectors enable acquisitions with many projections at low overall patient dose as compared with competing detector technologies.

Following acquisition of the image data, tomosynthesis techniques include reconstruction of images at various "slices" through the subject. Reconstruction algorithms permit reconstruction of many such slices at different spatial planes, typically parallel to the imaging plane of the detector. Such slices contain different anatomies located at various heights above the detector with underlying and overlying structures being generally suppressed. The generation of slices from projection images typically contains a chain of processing and operations. It should be noted that the term "projection" generally refers to a specific geometry or positioning of the X-ray source with respect to the subject and detector, many such projections being used in generating the slices as noted above.

Processing and operations used to generate slices from projection images in tomosynthesis include, but are not limited to, standard pre-processing steps, special pre-processing steps, reconstruction steps, and post-processing operations. Standard pre-processing operations include detector corrections, such as for gain, offset, bad pixels in the detector, and so forth. These may also include correction for geometry distortions, log transformation to store a "film-like look" and so forth. Special pre-processing steps may include bad detector edge correction, padding, beam hardening correction, off-focal radiation correction, reference normalization, and so forth. Reconstruction steps and algorithms may also vary. Many such algorithms are based on filtered back-projection principles, such as shift and add techniques, generalized filtered back-projection techniques, order statistics back-projections, and so forth. Algorithms based on back-projection filtering principles in which back-projection is performed first followed by 2D/3D filtering, and algorithms based on minimum-norm solutions are also available. These include algorithms known in the field as ART, DART, MITS, TACT, Fourier-based reconstruction, objective function-base reconstruction, ML, MAP, and so forth, and combinations of these. Post-processing may include various types of image and contrast enhancement, such as tissue equalization, thickness compensation, brightness and white balancing, and additional artifact management routines.

In general, back-projection is the favored process to generate tomosynthesis slices, and is typically used in many of the reconstruction algorithms listed above. In back-projection, pixel intensity values are assigned to computed pixels of slices at the various levels above the imaging plane to form the slice images from the projection data. This is generally done by assigning values of pixels at each slice by dividing the intensity of the pixels in the projection data by the number of slices to be reconstructed. This uniform view weighting, however, causes many problems and inconsistencies in the reconstructed images. These issues may, then, result in artifacts such as wavy patterns in the reconstructed images, general fall off of intensity values near edges of the images, and ghost-like images at elevations above, image plane where the subject cannot have been located (i.e. beyond the physical limits of the subject being imaged). There is a need, therefore, for improved techniques for tomosynthesis image data processing. There is a particular need for a technique which accounts for a wide range of factors which can render reconstructed images inconsistent or otherwise degrade the images. Needs exist, for example, for techniques that reduce the fall-off of data near the edges of slice images, that reduce the assignment of values beyond the limits of the subject, and that reduce the deformity or inconsistency of the resulting data that can result from many factors affecting the underlying projection data.

BRIEF DESCRIPTION OF THE INVENTION

The present invention provides novel techniques for processing tomosynthesis data designed to respond to these needs. These techniques may be used in a wide range of processing steps, but are particularly well-suited to back-projection processes of the type used in many tomosynthesis image reconstruction approaches. The techniques provide for weighting of views in tomosynthesis which is non-linear for one or several reasons. The technique may be based, for example, upon creation of weighting maps which may include weights that are specific for each pixel in the various slices. A count map may be included in a processing, along with a slice weighting function, and a projection weighting function. These maps may be computed in advance of imaging and used in reconstruction, or may be adapted for specific imaging implementations and exams.

DETAILED DESCRIPTION OF SPECIFIC EMBODIMENTS

Figure 1:
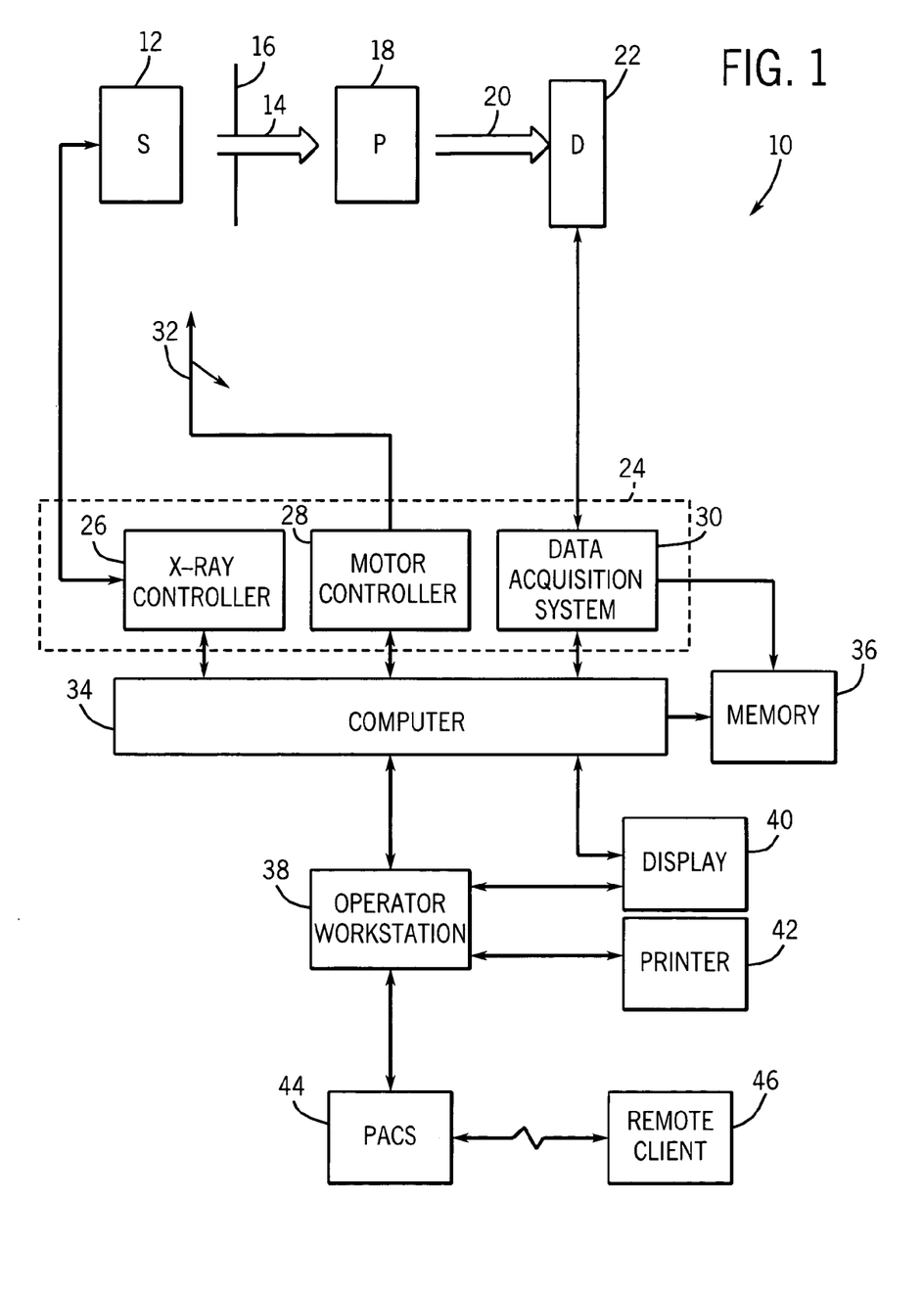
FIG. 1 is a diagrammatical representation of an exemplary tomosynthesis system wherein non-uniform view weighting is implemented in accordance with the present techniques.

FIG. 1 is a diagrammatical representation of an exemplary tomosynthesis system, designated generally by the reference numeral 10, for acquiring, processing and displaying tomosynthesis images, including images of various slices through a subject of interest in accordance with the present techniques. In the embodiment illustrated in FIG. 1, tomosynthesis system 10 includes a source 12 of X-ray radiation which is movable generally in a plane, or in three dimensions. In the exemplary embodiment, the X-ray source 12 typically includes an X-ray tube and associated support and filtering components.

A stream of radiation 14 is emitted by source 12 and passes into a region of a subject, such as a human patient 18. A collimator 16 serves to define the size and shape of the X-ray beam 14 that emerges from the X-ray source toward the subject. A portion of the radiation 20 passes through and around the subject, and impacts a detector array, represented generally by reference numeral 22. Detector elements of the array produce electrical signals that represent the intensity of the incident X-ray beam. These signals are acquired and processed to reconstruct an image of the features within the subject.

Source 12 is controlled by a system controller 24 which furnishes both power and control signals for tomosynthesis examination sequences, including position of the source 12 relative to the subject 18 and detector 22. Moreover, detector 22 is coupled to the system controller 24 which commands acquisition of the signals generated by the detector 22. The system controller 22 may also execute various signal processing and filtration functions, such as for initial adjustment of dynamic ranges, interleaving of digital image data, and so forth. In general, the system controller 24 commands operation of the imaging system to execute examination protocols and to process acquired data. In the present context, the system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, the system controller 24 includes an X-ray controller 26 which regulates generation of X-rays by the source 12. In particular, the X-ray controller 26 is configured to provide power and timing signals to the X-ray source. A motor controller 28 serves to control movement of a positional subsystem 32 that regulates the position and orientation of the source with respect to the subject and detector. The positional subsystem may also cause movement of the detector, or even the patient, rather than or in addition to the source. It should be noted that in certain configurations, the positional subsystem 32 may be eliminated, particularly where multiple addressable sources 12 are provided. In such configurations, projections may be attained through the triggering of different sources of X-ray radiation positioned accordingly. Finally, in the illustration of FIG. 1, detector 22 is coupled to a data acquisition system 30 that receives data collected by readout electronics of the detector 22. The data acquisition system 30 typically receives sampled analog signals from the detector and converts the signals to digital signals for subsequent processing by a computer 34. Such conversion, and indeed any preprocessing, may actually be performed to some degree within the detector assembly itself.

Computer 34 is typically coupled to the system controller 24. Data collected by the data acquisition system 30 is transmitted to the computer 34 and, moreover, to a memory device 36. Any suitable type of memory device, and indeed of a computer, may be adapted to the present technique, particularly processors and memory devices adapted to process and store large amounts of data produced by the system. Moreover, computer 34 is configured to receive commands and scanning parameters from an operator via an operator workstation 38, typically equipped with a keyboard, mouse, or other input devices. An operator may control the system via these devices, and launch examinations for acquiring image data. Moreover, computer 34 is adapted to perform reconstruction of the image data as discussed in greater detail below. Where desired, other computers or workstations may perform some or all of the functions of the present technique, including post-processing of image data simply accessed from memory device 36 or another memory device at the imaging system location or remote from that location.

In the diagrammatical illustration of FIG. 1, a display 40 is coupled to the operator workstation 38 for viewing reconstructed images and for controlling imaging. Additionally, the image may also be printed or otherwise output in a hardcopy form via a printer 42. The operator workstation, and indeed the overall system may be coupled to large image data storage devices, such as a picture archiving and communication system (PACS) 44. The PACS 44 may be coupled to a remote client, as illustrated at reference numeral 46, such as for requesting and transmitting images and image data for remote viewing and processing as described herein. It should be further noted that the computer 34 and operator workstation 38 may be coupled to other output devices which may include standard or special-purpose computer monitors, computers and associated processing circuitry. One or more operator workstations 38 may be further linked in the system for outputting system parameters, requesting examinations, viewing images, and so forth. In general, displays, printers, workstations and similar devices supplied within the system may be local to the data acquisition components or, as described above, remote from these components, such as elsewhere within an institution or in an entirely different location, being linked to the imaging system by any suitable network, such as the Internet, virtual private networks, Ethernets, and so forth.

Figure 2:
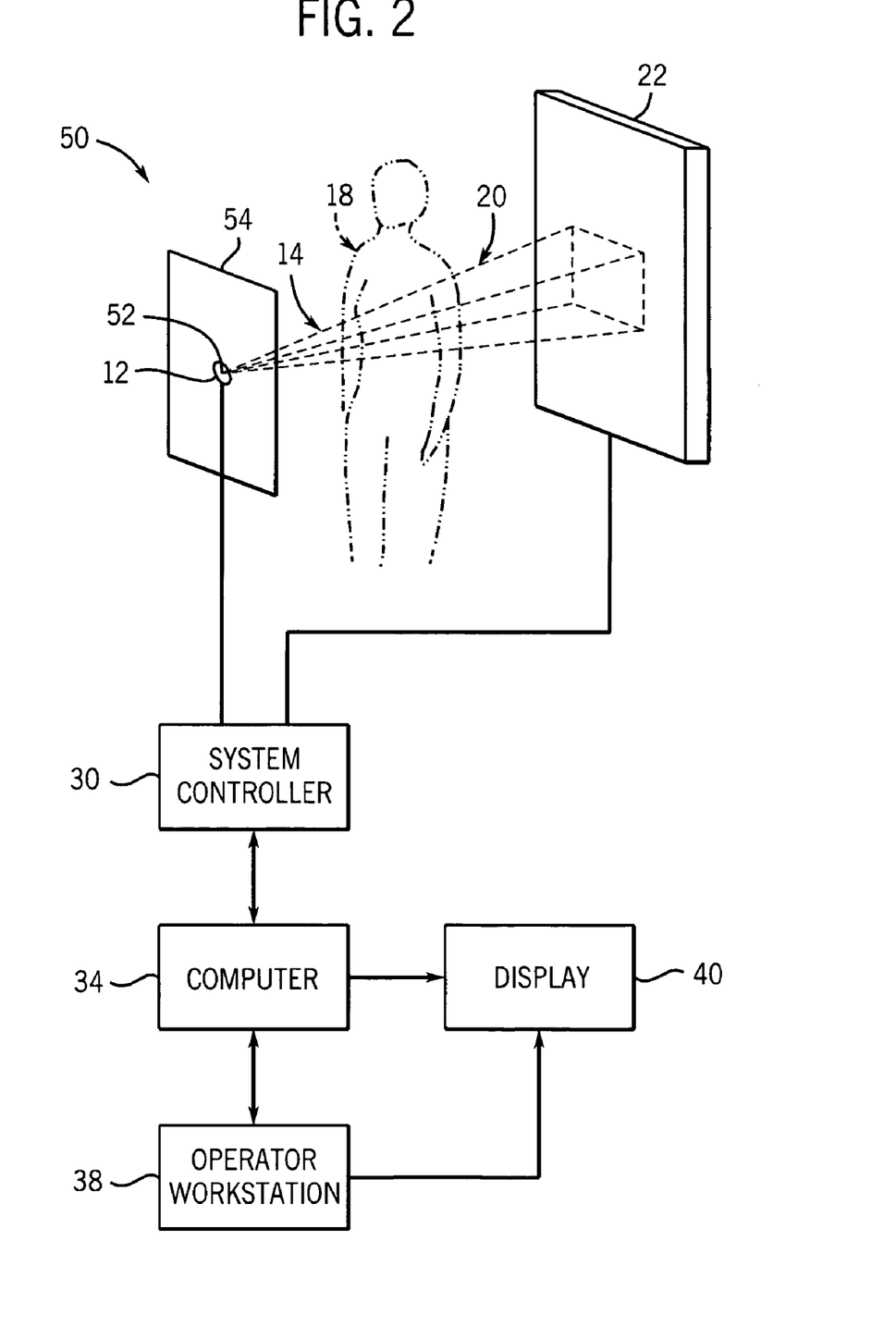
FIG. 2 is a diagrammatical representation of a physical implementation of the system of FIG. 1.

Referring generally to FIG. 2, an exemplary implementation of a tomosynthesis imaging system of the type discussed with respective of FIG. 1 is illustrated. As shown in FIG. 2, an imaging scanner 50 generally permits interposition of a subject 18 between the source 12 and detector 22. Although a space is shown between the subject and detector 22 in FIG. 2, in practice, the subject may be positioned directly before the imaging plane and detector. The detector may, moreover, vary in size and configuration. The X-ray source 12 is illustrated as being positioned at a source location or position 52 for generating one or a series of projections. In general, the source is movable to permit multiple such projections to be attained in an imaging sequence. In the illustration of FIG. 2, a source plane 52 is defined by the array of positions available for source 12. The source plane 54 may, of course, be replaced by three-dimensional trajectories for a movable source. Alternatively, two-dimensional or three-dimensional layouts and configurations may be defined for multiple sources which may or may not be independently movable.

In typical operation, X-ray source 12 projects an X-ray beam from its focal point toward detector 22. A portion of the beam 14 that traverses the subject 18, results in attenuated X-rays 20 which impact detector 22. This radiation is thus attenuated or absorbed by the internal features of the subject, such as internal anatomies in the case of medical imaging. The detector is formed by a plurality of detector elements generally corresponding to discrete picture elements or pixels in the resulting image data. The individual pixel electronics detect the intensity of the radiation impacting each pixel location and produce output signals representative of the radiation. In an exemplary embodiment, the detector consists of an array of 2048×2048. Other detector configurations and resolutions are, of course, possible. Each detector element at each pixel location produces an analog signal representative of the impending radiation, that is converted to a digital value for processing.

Source 12 is moved and triggered, or distributed sources are similarly triggered, to produce a plurality of projections or images from different source locations. These projections are produced at different view angles and the resulting data is collected by the imaging system. In an exemplary embodiment, the source 12 is positioned approximately 180 cm from the detector, in a total range of motion of the source between 31 cm and 131 cm, resulting in a 5° to 20° movement of the source from a center position. In a typical examination, many such projections may be acquired, such as in excess of 50 or 60, although this number may vary.

Either directly at the imaging system, or in a post-processing system, data collected by the system is manipulated by performing mathematical operations designed to compute the locations at which objects are located in the subject that produced the attenuation of the X-ray beam sensed by the detector. This overall process is generally referred to as back-projection. It has been found that a number of problems exist in conventional back-projection as applied to tomosynthesis imaging. For example, such techniques do not typically account for the fact that different regions of different slices are traversed by radiation for certain projections and not others. Because the back-projection techniques typically assume that all reconstructed slices contribute equally to X-ray attenuation, however, degradation of image quality for certain slices occurs because this assumption is incorrect. Similarly, conventional techniques tend to result in an assumption that locations physically outside of a subject may have contributed to the X-ray attenuation. Similarly, the techniques assume that all projections, corresponding to various source and/or detector locations, are equally valid for all pixels in the projections. As discussed in greater detail below, these assumptions are corrected by the present technique by providing non-uniform weighting of views in the image reconstruction process. Details regarding the specific steps in image reconstruction are not provided herein separately, as these steps may be generally conventional in nature.

Figure 3:
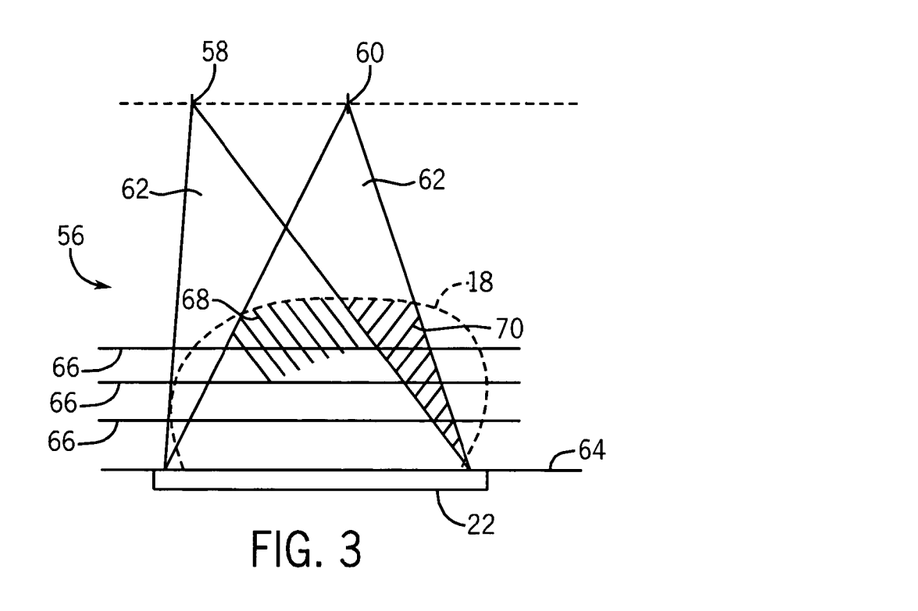
FIG. 3 is an elevational diagram of radiation paths during a tomosythesis image acquisition series illustrating issues involved in weighting of slice data accounted for through the present technique.

FIG. 3 illustrates an elevational view of a tomosynthesis system in which two projection configurations are illustrated. The projection configuration, generally represented by reference numeral 56, is illustrated as including two source positions 58 and 60, with source position 60 generally corresponding to a centralized source position with respect to detector 22, and source position 58 being offset from the center position. Each source position produces a beam 62 generally in a fan shape, which in actual practice may be a cone or controlled cone. The beam fans 62 impact detector 22 generally at an imaging plane 64. Above the imaging plane 64, various slices 66 may be constructed through the subject 18 to provide an indication of the internal features of the subject.

As can be seen in FIG. 3, the radiation emanating from source positions 58 and 60 intersect one another differently in different regions of the imaging volume. Because slices 66 divide the imaging volume, then, the radiation intersects different slices differently and in spatially different locations. As shown in FIG. 3, for example, in an intersecting region 68, radiation from source position 58 fully intersects radiation from source position 60. In an other region, generally a non-intersecting region 70, however, an upper slice 66 is not traversed by radiation originating at source position 58, but is traversed by radiation originating from source position 60.

Conventional back-projection reconstruction techniques would assume that attenuation of radiation from the various slices designated for reconstruction receive a contribution from objects at each slice position. However, as can be seen in FIG. 3, this is not the case. That is, all slices illustrated in the figure do contribute to attenuation of radiation from source positions 58 and 60 in the intersecting region 68, although within region 70, only radiation from source position 60 is attenuated by the features visible in the slices. It may also be noted from FIG. 3 that the surface area or portion of each projection in which the radiation intersects and does not intersect is not equal. That is, each slice has different regions of intersecting and non-intersecting radiation. It should also be noted that, in practice, many more projections are generally generated, resulting in many such regions of intersecting and non-intersecting radiation.

Figures 4, 5:
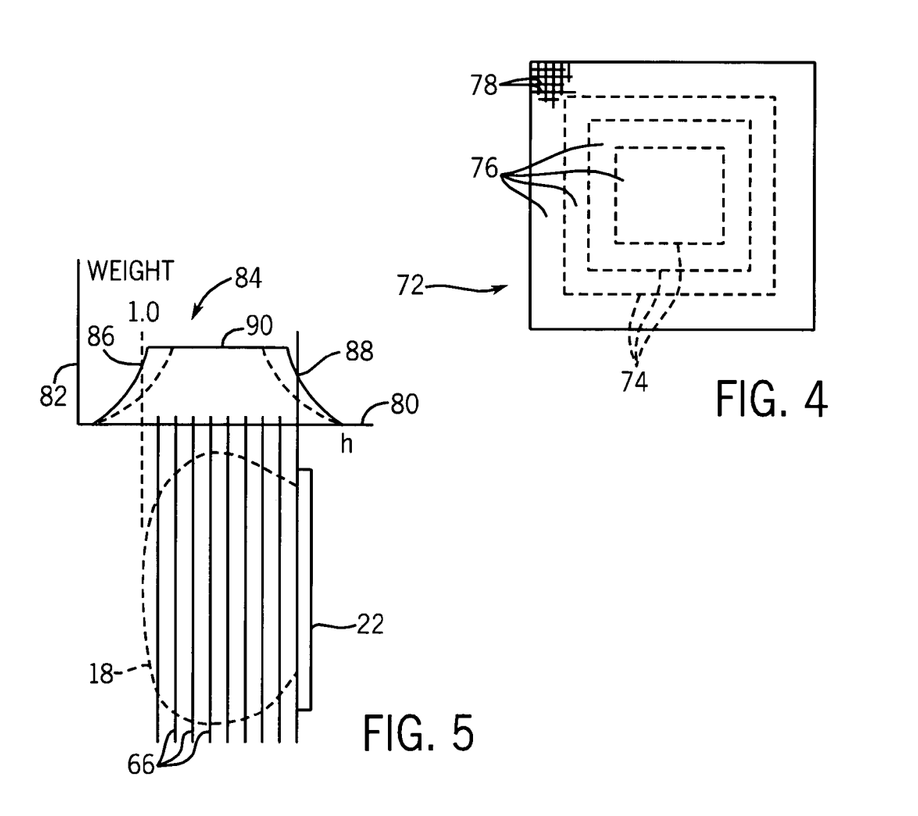
FIG. 4 is a plan view of an exemplary count map used to non-uniformly weight image data in accordance with the present technique.
FIG. 5 is a graphical illustration of a slice weighting technique used to account for physical limits of a subject being imaged.

The present technique accommodates such intersection and non-intersection of radiation by generating a count map for each slice. In general, the count map is a plan view, on a pixel-by-pixel basis, wherein each pixel is assigned a value corresponding to the number of times it is traversed by radiation from the various projections (i.e. source locations). The count maps, then, represent the number of back-projection paths of the radiation through each pixel at each slice level. FIG. 4 represents an exemplary slice map for an elevated slice. The slice map 72 will generally include boundaries 74 defined by counting or computing the number of times each individual pixel is traversed by radiation in the various projections. The boundaries, then, define regions 76 in which pixels have the same count. Again, the values are assigned on a pixel-by-pixel basis for various pixels of the slice image as represented generally by reference numeral 78.

Several aspects of the count maps are worth noting. First, it is generally anticipated that higher counts will be present in center regions of the map as compared to regions that are closer to the detector boundary, due to the fact that outlying source positions generally still traverse the central region of each slice. Similarly, it will be anticipated that lower slices would have larger regions of higher counts than upper slices due to the angles of the projections and the fact that the projections generally are directed toward the portion of the imaging plane in which the detector is located. As will be appreciated by those skilled in the art, this is true only for stationary detectors, to minimize the total "low count" area or volume, the detector could move such that the center slice has the biggest high-count region. Also, the particular contours and locations of boundaries 74 and of regions 76 may vary considerably depending upon the arrangement of the source positions giving rise to the various projections.

In the present technique, the count map 72 for each slice is utilized to weight the contribution of pixels in each to the sensed X-ray attenuation. That is, regions of the count map having the highest value are considered to have fully contributed to the X-ray attenuation, where as counts that are lower are considered to contribute less, and are therefore weighted a lower amount in reconstruction. The weighting based upon the account map may be linear, that is, may vary proportionally with the count number, or it may also be non-linear.

Further non-uniform weighting is provided by the present technique to account for a false assumption in conventional back-projection that results in contribution of regions entirely outside of the subject to sensed X-ray attenuation. FIG. 5 generally represents a slice weighting technique implemented by the present processing. As shown in FIG. 5, subject 18 is positioned immediately adjacent to detector 22, and slices 66 are to be computed by back-projection. As will be appreciated by those skilled in the art, however, conventional techniques may result in ghost-like images being computed for regions far outside (e.g. to the left of) subject 18. The present technique employs slice weighting in which non-uniform weighting factors are computed, particularly outside the anticipated or actual bounds of the subject. In the illustration of FIG. 5, the height above the imaging plane adjacent to detector 22 is indicated along in axis 80, and a weighting factor value is indicated along a vertical axis 82. The weighting function is represented by a trace 84 which varies in value with the height above the detector. In the illustrated embodiment, an upper ramp weighting region 86 is defined which provides weighting values down to a null value at a desired distance from the upper limits of the subject. A similar lower ramp weighting region 88 is provided near the lower bound of the subject. A central weighting portion 90, which includes the slices of interest, has a uniform or generally uniform value of unity. It is anticipated that certain optimization of the non-uniform slice weighting values may be determined, and in the context of medical imaging, that the reduction from a value of unity to a null value may begin at, just below or just above the skin line of the subject. As discussed below, such non-uniform view weighting may be used with or separately from the count map weighting described above.

Figure 6:
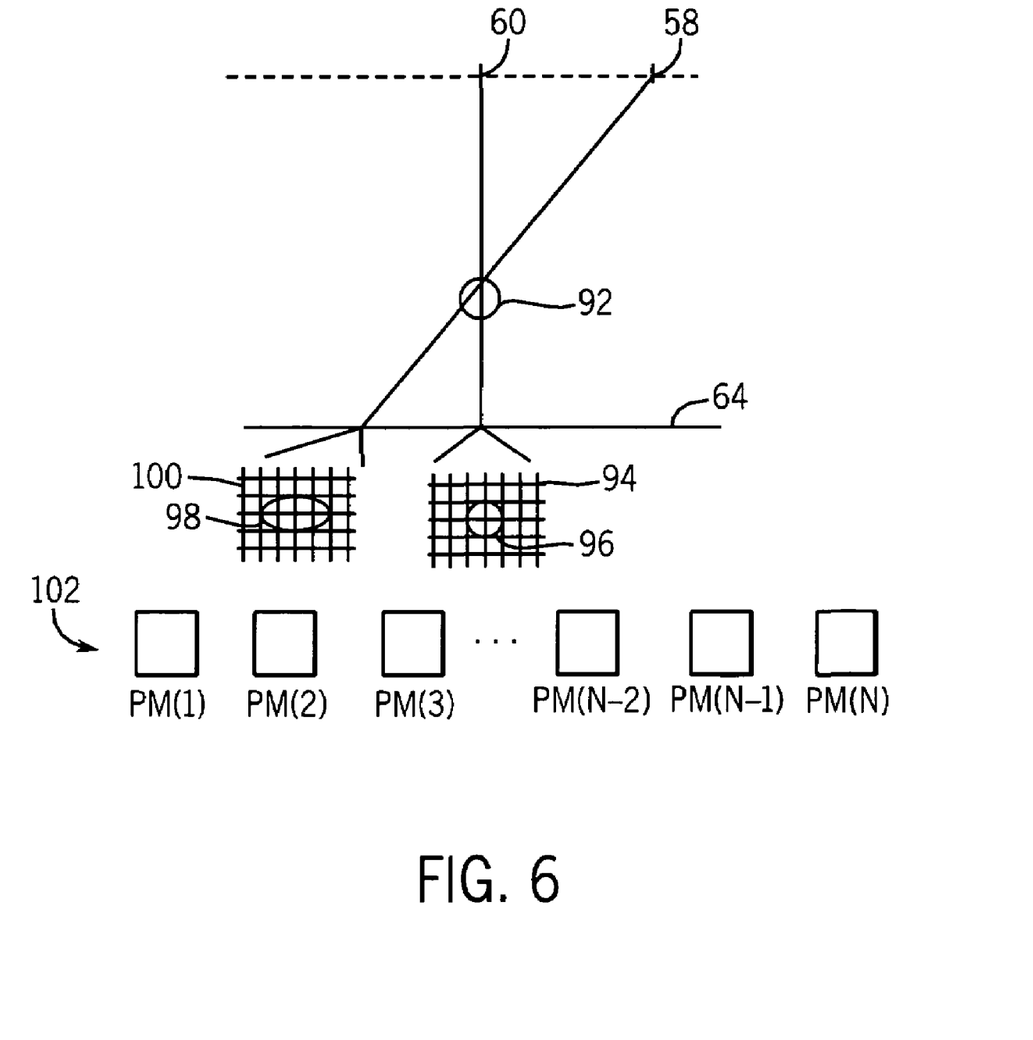
FIG. 6 is an illustration of projection weighting masks used in the present technique for accounting for variations in response from a tomosynthesis system in various projections.

A further issue with a conventional tomosynthesis back-projection involves different system performance at different projections. FIG. 6 illustrates schematically this point. As shown in FIG. 6, for two different source locations, resulting in two different projections, an object 92 may appear substantially differently. In the example of FIG. 6, for example, a spherical object 92 may appear in a generally central projection 94 as generally circular, as indicated at reference numeral 96. As the source is moved to other positions to produce other projections, such as projection 98 in FIG. 6, the same object may appear deformed or distorted, such as a spherical object projecting as a generally elliptical shape 100 in an outline projection as shown in FIG. 6. In general, such distortions may be caused by a wide range of factors. These factors may be a function of the source position, the detector performance, particularly near the edges of the detector, the geometry of the system, the distance traversed by X-rays in the various projections, beam scatter, beam hardening, and so forth. Conventional back-projection techniques, however, do not account for such system variation. All projections in conventional techniques are considered to be equally valid for all pixel locations when considered for computation of the appropriate pixel values in the various reconstructed slices. It should be noted that the projection weighting can also be used to manage artifacts. For example, an initial segmentation of the imaged object could be made (e.g., into chest wall and lung tissues), with the resulting regions receiving different weights (e.g., regions of interest, such as lung tissues receiving higher weights). This could reduce artifacts at the skin line in medical images.

In the present technique, on the other hand, individual projection weighting maps are generated for each of the projections utilized to produce the reconstructed slice images. The projection maps may be generated as a calibration step, and stored for later use in reconstruction of the slice images. In general, it is contemplated that such projection maps will be generated for each projection utilized in the reconstruction technique, as indicated generally at reference numeral 102 in FIG. 6.

The various non-uniform weighting approaches described herein may be used together or separately. In general, the resulting weighting will change the computed contribution of the various slice features, slices and projections to the computed pixel values for each re-projected slice image. The general relationship between the non-uniform weighting factors discussed above may be represented by the relationship $$I_i = W_s[I_i W_{pi}/W_{ci}]:$$

where $I_i$ is the value of each individual pixel in the reconstructed slice image, $W_s$ is the slice weighting factor for each individual slice, $W_{pi}$ is the projection map weighting factor for each individual pixel in each projection, and $W_{ci}$ is the count map weighting factor for each pixel in each individual slice. Note that $(I_i W_{pi})$ has summed up all contributions from different projections and is appropriately normalized. The use of the count map generally will cause a non-homogeneous look in the resulting images to be compensated for during back-projection. The use of slice weighting will cause out-of-plane artifacts due to limited projection angles to be suppressed for regions near or beyond the limits of the subjects of interest. Finally, the use of projection weighting will account for non-uniformities in the tomography system response.

The concept of back-projection reconstruction with view weighting in accordance with the present techniques may be thought of as consisting of several steps. First, multiple digital tomosynthesis projections are acquired and stored, these projections are then accessed for processing. One, two and three-dimensional view weighting functions (masks or maps) for projection, slice and volumes of interest are then computed. The view weighting functions generally consist of spatially-varying values or weights. Examples provided in the present context include a count map where entries in the map represent the number of times that back-projection rays intersect pixels at various slice elevations. Functions, such as box functions, ramping functions, for smooth functions are applied for contributions of various slices to X-ray attenuation. Finally, overall system response is accommodated by production of projection maps used for weighting in the reconstruction process.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for processing tomosynthesis image data comprising:
    identifying a plurality of non-uniform weighting factors for use in back-projection processing of image data representative of X-ray attenuation by a subject of interest at multiple source positions corresponding to multiple projections;
    accessing the image data; and
    back-projecting image data by application of the non-uniform weighting factors.

2. The method of claim 1, wherein the weighting factors are based on counts of a number of times pixels at image slice locations are traversed by radiation from multiple different source positions during acquisition of the image data.

3. The method of claim 2, comprising generating a count map representative of the counts.

4. The method of claim 1, wherein the weighting factors are based on a relative elevation of image slices from a detector plane.

5. The method of claim 4, wherein the weighting factors are determined by application of a weighting function having values of unity for slice locations generally within a subject to be imaged and values declining from unity near limits of the subject.

6. The method of claim 5, wherein the values decline to a null value to suppress computed contribution of regions outside the subject to be imaged to sensed x-ray attenuation.

7. The method of claim 1, wherein the weighting factors are based upon specific projections generated by a system from which the image data is acquired.

8. The method of claim 7, wherein a separate set of weighting factors are generated for each projection.

9. The method of claim 8, wherein the weighting factors are determined during a calibration procedure for the system prior to acquisition of the image data.

10. The method of claim 1, wherein the weighting factors include at least two different types of factors selected from a group consisting of count weighting factors, slice weighting factors and projection weighting factors.

11. A method for processing tomosynthesis image data comprising:
    determining count weighting factors representative of a number of times pixels of image slices are traversed by radiation from a plurality of source positions during imaging;
    determining slice weighting factors for weighting image slices within a subject differently from locations near and beyond limits of the subject;
    determining projection weighting factors accounting for differences in system response for a plurality of projections corresponding to the plurality of source positions; and
    back-projecting tomosynthesis image data based upon the count weighting factors, the slice weighting factors and the projection weighting factors.

12. The method of claim 11, comprising generating a count map representative of the counts, a count map being generated for each image slice to be back-projected.

13. The method of claim 11, wherein the slice weighting factors are determined by application of a weighting function having values of unity for slice locations generally within a subject to be imaged and values declining from unity near limits of the subject.

14. The method of claim 13, wherein the values decline to a null value to suppress computed contribution of regions outside the subject to be imaged to sensed x-ray attenuation.

15. A method for processing tomosynthesis image data comprising:
    determining count weighting factors representative of a number of times pixels of image slices are traversed by radiation from a plurality of source positions during imaging;
    accessing the image data representative of X-ray attenuation of a subject of interest at multiple source positions corresponding to multiple projections; and
    back-projecting image data by application of the count weighting factors.

16. A method for processing tomosynthesis image data comprising:
    determining slice weighting factors for weighting image slices within a subject differently from locations near and beyond limits of the subject;
    accessing the image data representative of X-ray attenuation by a subject of interest at multiple source positions corresponding to multiple projections; and
    back-projecting image data by application of the slice weighting factors.

17. A method for processing tomosynthesis image data comprising:
    determining projection weighting factors accounting for differences in system response for a plurality of projections corresponding to the plurality of source positions;
    accessing the image data representative of X-ray attenuation by a subject of interest at multiple source positions corresponding to multiple projections; and
    back-projecting image data by application of the projection weighting factors.

18. A system for processing tomosynthesis image data comprising:
    means for identifying a plurality of non-uniform weighting factors for use in back-projection processing of image data representative of X-ray attenuation by a subject of interest at multiple source positions corresponding to multiple projections;
    means for accessing the image data; and
    means for back-projecting image data by application of the non-uniform weighting factors.

19. A system for processing tomosynthesis image data comprising:
    means for determining count weighting factors representative of a number of times pixels of image slices are traversed by radiation from a plurality of source positions during imaging;
    means for determining slice weighting factors for weighting image slices within a subject differently from locations near and beyond limits of the subject;

means for determining projection weighting factors accounting for differences in system response for a plurality of projections corresponding to the plurality of source positions; and means for back-projecting tomosynthesis image data based upon the count weighting factors, the slice weighting factors and the projection weighting factors.

20. A computer program for processing image data comprising:

at least one machine readable medium; and machine readable code stored on the at least one medium for carrying out routines for identifying a plurality of non-uniform weighting factors for use in back-projection processing of image data representative of X-ray attenuation by a subject of interest at multiple source positions corresponding to multiple projections; accessing the image data, and back-projecting image data by application of the non-uniform weighting factors.

21. A computer program for processing image data comprising:

at least one machine readable medium; and machine readable code stored on the at least one medium for carrying out routines for determining count weighting factors representative of a number of times pixels of image slices are traversed by radiation from a plurality of source positions during imaging, determining slice weighting factors for weighting image slices within a subject differently from locations near and beyond limits of the subject, determining projection weighting factors accounting for differences in system response for a plurality of projections corresponding to the plurality of source positions, and back-projecting tomosynthesis image data based upon the count weighting factors, the slice weighting factors and the projection weighting factors.

* * * * *